(12) United States Patent
Li et al.

(10) Patent No.: US 8,891,735 B2
(45) Date of Patent: Nov. 18, 2014

(54) AUTO GRID MOVING DEVICE FOR DIAGNOSTIC X RAY TABLE

(75) Inventors: Yuqing Li, Beijing (CN); Fusheng Li, Beijing (CN); Yingjie Jia, Beijing (CN); Weining Xi, Beijing (CN)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 173 days.

(21) Appl. No.: 13/436,842

(22) Filed: Mar. 31, 2012

(65) Prior Publication Data

US 2012/0275570 A1    Nov. 1, 2012

(30) Foreign Application Priority Data

Mar. 31, 2011    (CN) .......................... 2011 1 0096091

(51) Int. Cl.
*G21K 1/00*    (2006.01)
*A61B 6/00*    (2006.01)
*A61B 6/04*    (2006.01)

(52) U.S. Cl.
CPC ............... *A61B 6/583* (2013.01); *A61B 6/0457* (2013.01); *A61B 6/4291* (2013.01)
USPC ......................................................... 378/155

(58) Field of Classification Search
USPC .......................................................... 378/155
See application file for complete search history.

(56) References Cited

U.S. PATENT DOCUMENTS

| 2,767,323 | A | * | 10/1956 | Stava et al. ..................... 378/155 |
| 4,118,116 | A | * | 10/1978 | Koontz et al. ................... 378/28 |
| 4,542,521 | A | * | 9/1985 | Hahn et al. ..................... 378/155 |
| 5,402,462 | A | * | 3/1995 | Nobuta ............................ 378/20 |
| 2001/0022833 | A1 | * | 9/2001 | Kobayashi ..................... 378/177 |

FOREIGN PATENT DOCUMENTS

JP    2001154299 A  *  6/2001

* cited by examiner

*Primary Examiner* — Glen Kao
(74) *Attorney, Agent, or Firm* — GE Global Patent Operation; Marc A. Vivenzio

(57) ABSTRACT

An auto grid moving apparatus for an X ray imaging device is provided. The apparatus includes: a grid; a grid holder on which the grid is disposed; a fixing base; and a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move.

13 Claims, 4 Drawing Sheets

AUTO GRID MOVING DEVICE FOR DIAGNOSTIC X RAY TABLE

BACKGROUND OF THE INVENTION

1. Field of the Invention

The field of the invention relates to the configuration of a grid for an X ray imaging device.

2. Description of Related Art

The grid for an X ray imaging device is generally mountable onto an X ray detector housing, from which the operator can push in or pull out the grid as needed. Usually, the operator has to pull out the grid from the detector housing of the X ray imaging device bed for pediatric and extremity X ray inspections; and push back in for other X ray inspections. This configuration and operation suffers from several deficiencies. First, the operator may sometimes have difficulty pushing in or pulling out the grid as a result of not being able to locate the grid-in slot when performing such operation. The operation of this configuration is also time consuming. Meanwhile, a grid docking device takes up space. Furthermore, frequent pushing in and pushing out of the grid may cause damage.

To solve the aforementioned problems, an auto grid moving apparatus is provided. The grid can move in the area of X ray detector automatically, and can be driven automatically according to X ray exposure exam parameters, thereby replacing the aforementioned manual pushing in and out operation of the grid.

BRIEF SUMMARY OF THE INVENTION

According to an embodiment of the present invention, an auto grid moving apparatus for an X ray imaging device is provided. The apparatus includes: a grid; a grid holder on which the grid is disposed; a fixing base; and a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move.

According to another embodiment of the present invention, a bed of an X ray imaging device is provided. The bed includes: a table; an X ray detector holder housing disposed beneath the table; table frames at two ends of the table; and an auto grid moving apparatus located between the underneath of the table and the X ray detector holder housing. The auto grid moving apparatus includes: a grid; a grid holder on which the grid is disposed; a fixing base fixed beneath the table; and a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move. The auto grid moving apparatus is configured to drive the grid back and forth between the X ray detector housing and the table According to yet another embodiment of the present invention, an X ray imaging device is provided. The X ray imaging device includes an auto grid moving apparatus that includes: a grid; a grid holder on which the grid is disposed; a fixing base; and a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move.

BRIEF DESCRIPTION OF THE DRAWINGS

The accompanying drawings illustrate exemplary embodiments of the present invention in which.

DETAILED DESCRIPTION OF THE INVENTION

The present disclosure will describe embodiments of the present invention, however, the present disclosure is not meant to be limited by the embodiments.

The embodiments of the present invention will be described in detail in combination with the figures, wherein the embodiments are not meant to limit the present invention, and wherein like numbers in the figures represent like parts.

Figure 1:
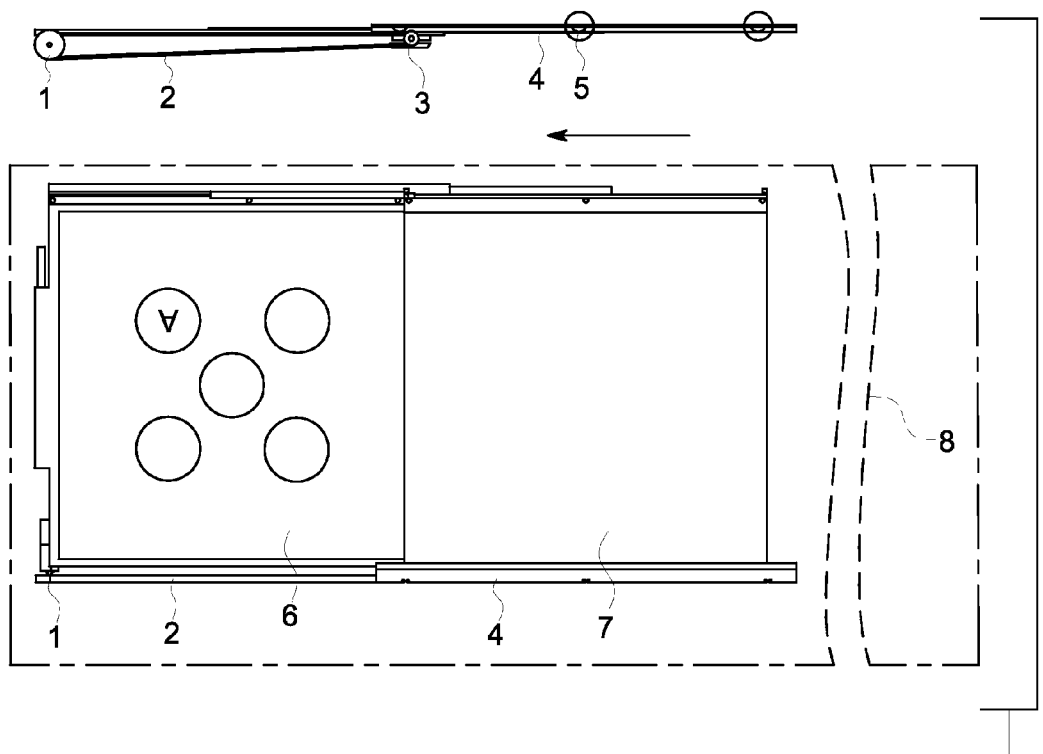
FIG. 1 shows a front view and top view of an auto grid moving apparatus according to an embodiment of the present invention.

FIG. 1 shows the front view (top of FIG. 1) and top view (bottom of FIG. 1) of an auto grid moving apparatus. The auto grid moving apparatus is located beneath a table 8. A grid 7 is driven by the auto grid moving apparatus and is able to move back and forth between the table 8 and an ion chamber 6 beneath the table 8. The apparatus makes use of a double sided timing belt 2. The timing belt 2 gears with two timing wheels 1 and 3 at two ends of its inner side face, wherein a motor is disposed on one of the timing wheels 1 to drive the timing belt 2. The outer side face of the timing belt 2 also gears with a grid holder 4 and another three semi-circular timing wheels 5 are fixed on the grid holder 4. The motor drives the timing wheel 1, thereby moving the timing belt 2 to drive the grid holder 4 to move towards the same direction. The grid holder 4 in turn moves the grid 7. The range of the movement can be triple the distance between the two timing wheels 1 and 3 (refer to top view).

Figure 2:
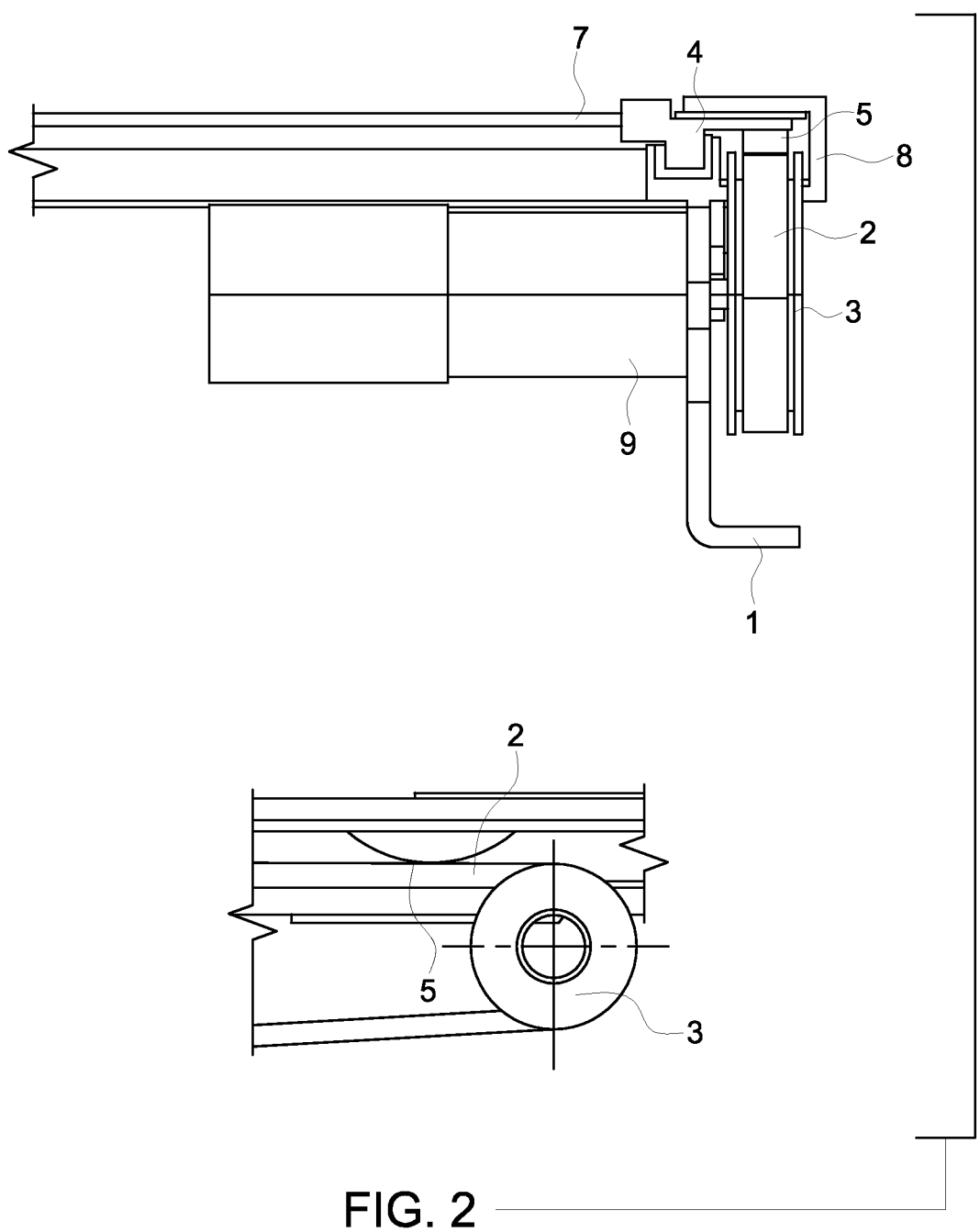
FIG. 2 shows a left side view of the auto grid moving apparatus and a front view of the semi-circular timing wheel part thereof according to an embodiment of the present invention.

FIG. 2 shows the left side view of the auto grid moving apparatus and the front view of the semi-circular timing wheel part thereof.

When the grid 7 needs to be moved to the area of X ray detector (or ion chamber 6), the double sided timing belt 2 is driven by the motor 9 disposed on the timing wheel 3 at one end thereof, thereby driving the timing wheel 3 at the other end to rotate. Meanwhile the teeth on the timing belt 2 engage with the semi-circular timing wheels 5 on the grid holder 4, and the movement of the timing belt 2 moves the gird holder 4 attached to the semi-circular timing wheels 5 through the semi-circular timing wheels 5.

In order to move the grid holder 4 as required, a guide rail 8 is disposed adjacent to the double sided timing belt 2 to constrain the moving direction of the grid holder 4. The guide rail 8 constrains to the grid holder 4 at its upward, downward, leftward and rightward directions, thereby the grid holder 4 can only move in the forward and backward directions followed with the timing belt 2. The guide rail 8 is fixed to the base 10 of the auto grid moving apparatus.

Figure 3:
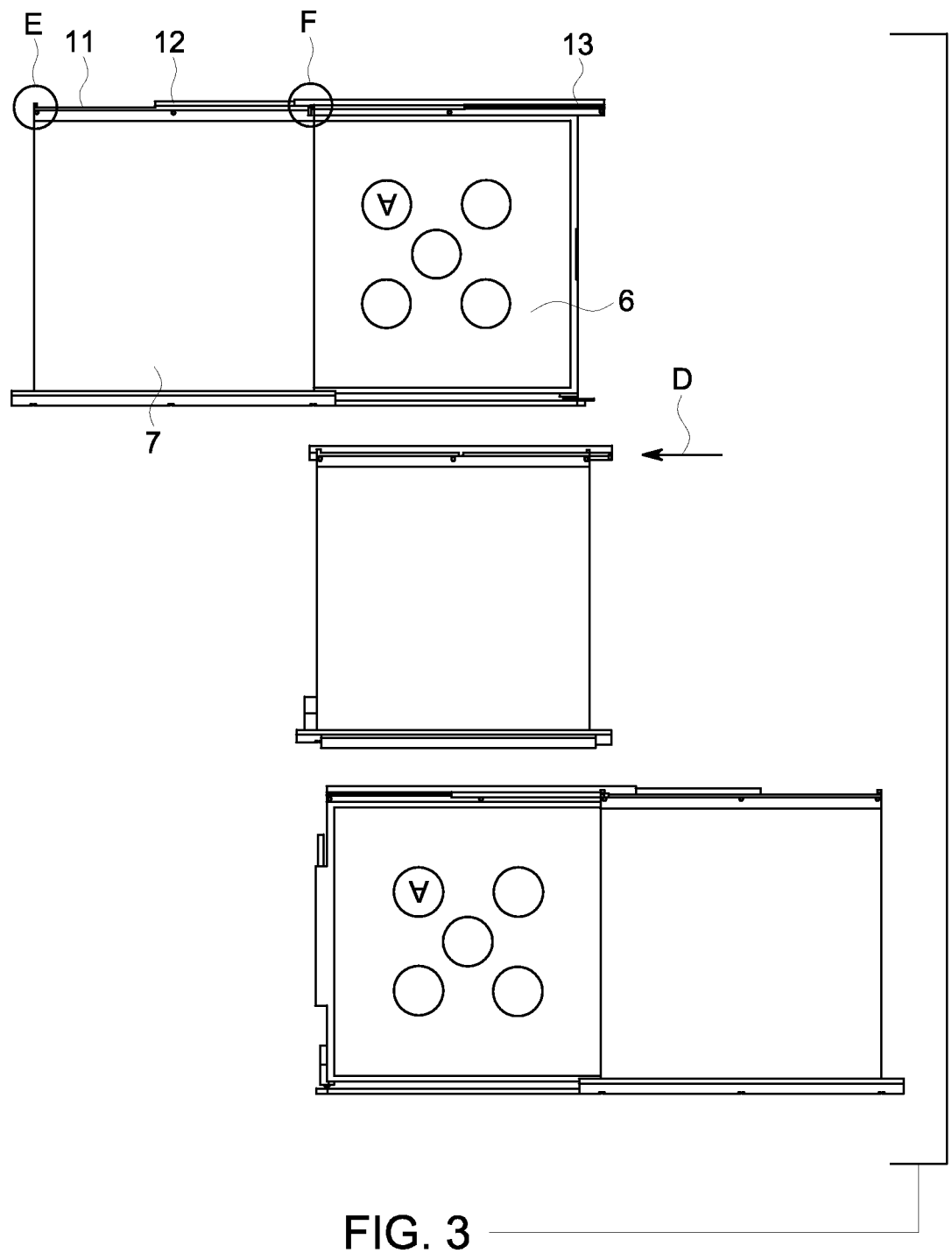
FIG. 3 shows a schematic view of the movement of the auto grid moving apparatus according to an embodiment of the present invention.

FIG. 3 shows the schematic view of the movement of the auto grid moving apparatus. The three drawings from top to bottom show the grid 7 moves to the left, center and right positions respectively, wherein the center position refers to a position that the grid 7 covers the area of the X ray detector (or the ion chamber 6).

When the grid 7 needs to be moved to the area of X ray detector (or ion chamber 6), the double sided timing belt 2 drives the grid holder 4 to move towards the right side, and keeps engaged with all of the three semi-circular timing wheels 5 on the grid holder 4 (the three semi-circular timing wheels corresponds to the left, center and right positions respectively in FIG. 3). When the grid 7 needs to be moved out of the area of X ray detector (or ion chamber 6), the double sided timing belt 2 drives the grid holder 4 to move towards the right or left side, and keeps engaged with at least one of the three semi-circular timing wheels 5 on the grid holder 4 (the positions of the three semi-circular timing wheels 5 are shown in FIGS. 1 and 2). The number of the semi-circular timing wheels 5 in engagement is determined by the length of the moving space of the auto grid moving apparatus left in the longitudinal direction of the bed of the X ray imaging device.

To prevent the grid holder 4 from moving out too much from the guide rail 8 and lead to deformation due to lack of support, a sliding grid support slider 12 is arranged to provide support for the grid 4 at the non-driving end (opposite to the driving end). The grid 7 is attached to a fixing plate 11 at the non-driving end, and support is provided by a guide rail base 13 at the non-driving end. The guide rail base 13 provides support to the grid 7 in a vertical direction when the grid 7 moves to the left or right side, so as to prevent the deformation of the grid holder 4 or the sliding grid support slider 12 caused by bending moment of the cantilever due to gravity. When the grid 7 moves to the center position, the sliding grid support slider 12 may partially protrude out of the guide rail base 13. Because the auto grid moving apparatus is mounted on the X ray detector housing, the X ray detector housing will be blocked by the table frame and automatically restore position when it reaches the end of the table.

Figure 4:
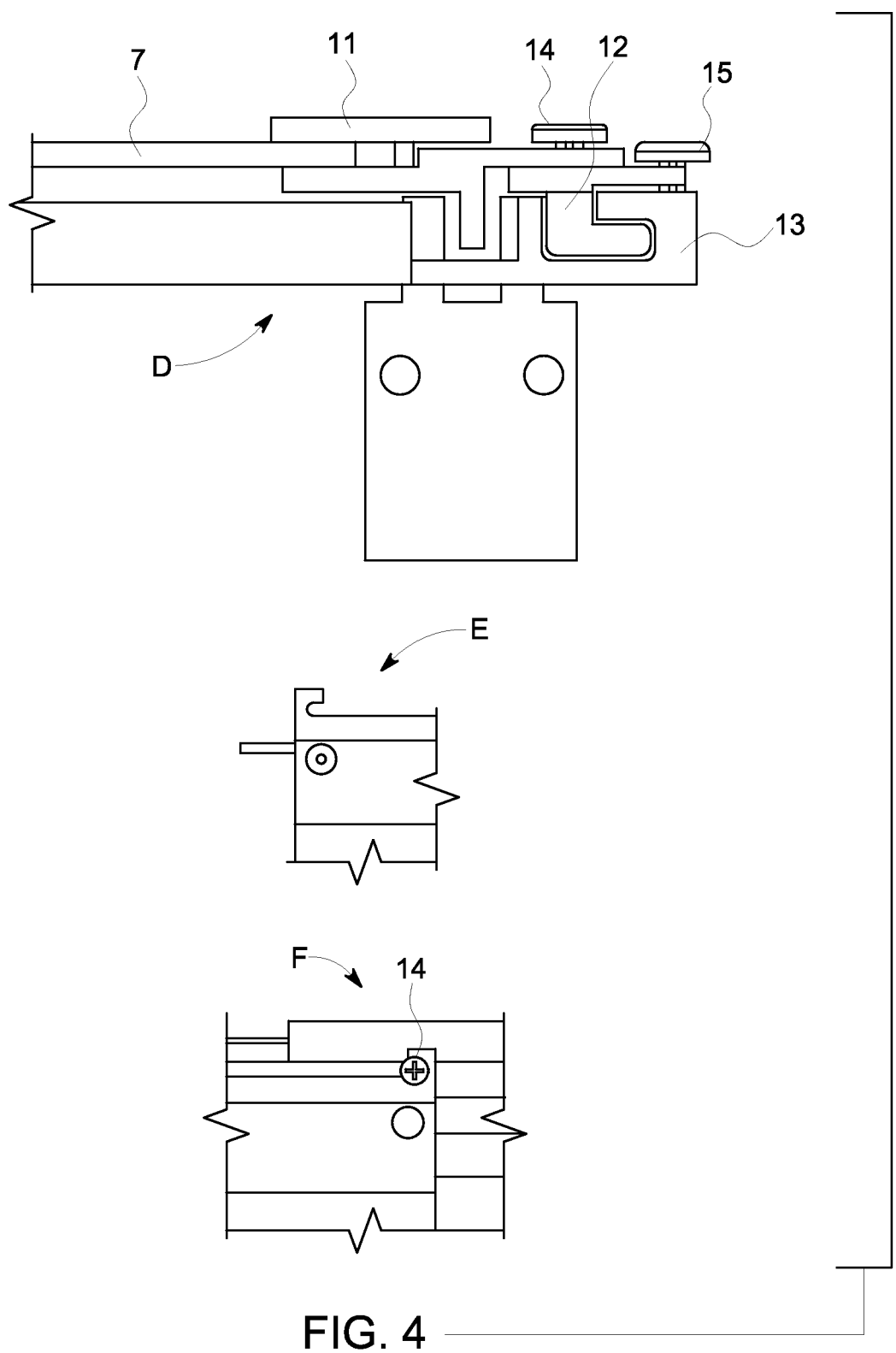
FIG. 4 shows a support configuration of the auto grid moving apparatus according to an embodiment of the present invention.

FIG. 4 shows the support configuration of the auto grid moving apparatus. When the grid 7 is at the left or right position, the grid holder 4 (refer to FIG. 2) is located above the guide rail base 13 at the driving end portion, and is supported by the sliding grid support slider 12 at the non-driving end. The sliding grid support slider 12 can move bi-directionally, and forms support to the grid 7. To make sure the sliding grid support slider 12 can move bi-directionally, as shown in the partial view D, there is a hard stopper at each of the two ends of the sliding support slider 12, cooperating with screw/bolt 15 on the guide rail base 13, the sliding support slider 12 always moves along the guide rail base 13 and protrudes at most half of its length, without getting detached. A screw/bolt 14 or a support block is provided at the middle portion of the sliding grid support slider 12, in the partial views E and F, the fixing plate 11 at the non-driving end has a hook at each of its two ends. When the grid 7 moves, the hook (screw/bolt) at one end will contact with the screw/bolt or the support block at the middle portion of the sliding grid support slider 12, pushing the sliding grid support slider 12 to slide on the guide rail base 13, thereby making sure at least half of the grid 7 is supported by the sliding grid support slider 12 when the grid 7 moves out of the imaging area completely.

The auto grid moving apparatus disclosed herein is applicable in an X ray imaging device, and further in other medical imaging diagnostic devices that require plug/pull or mount/unmount of the grid.

Embodiments of the present invention solve the problem that the operator has to manually pull out and push in the grid, which thereby facilitates the work of the operator. The auto grid moving apparatus also cancels the grid dock. Therefore, the structure is more compact and more reliable. Furthermore, the X ray imaging device according to embodiments of the present invention can achieve automatic mounting and unmounting of the grid with the control of the exposure parameters, thereby improving the efficiency of X ray inspection.

The aforementioned is only to disclose the invention by example, and is not intended to limit the invention. It should be noticed that, one skilled in the art may come up with improvements, changes and transformations without departing from the spirit of the invention, and such improvements, changes and transformations should be within the scope of the present application.

What is claimed is:

1. An auto grid moving apparatus for an X-Ray imaging device, the apparatus comprising:
    an X-ray grid;
    a grid holder on which the X-ray grid is disposed;
    a fixing base;
    a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move; and
    semi-circular timing wheels fixed on the grid holder, wherein the outer side face of the timing belt is geared with the grid holder through the semi-circular timing wheels.

2. The auto grid moving apparatus for X-Ray imaging device according to claim 1, further comprising a guide rail mounted adjacent to the double sided timing belt and fixed on the base of the auto grid moving apparatus, the guide rail being configured to constrain movement of the grid holder.

3. The auto grid moving apparatus for X-Ray imaging device according to claim 1, comprising three semi-circular timing wheels fixed at left, central and right sides of the grid holder respectively.

4. The auto grid moving apparatus for X-Ray imaging device according to claim 3, wherein the timing belt keeps engaged with all of the three semi-circular timing wheels on the grid holder when the X-Ray grid needs to be moved to the area of an X-Ray detector, and wherein the timing belt keeps engaged with at least one of the three semi-circular timing wheels on the grid holder when the X-Ray grid needs to be moved out of the area of the X-Ray detector.

5. An X-Ray imaging device comprising the auto grid moving apparatus of claim 1.

6. The X-Ray imaging device according to claim 5, wherein the position of the X-ray grid is automatically set by the auto grid moving apparatus according to an X-Ray exposure parameter.

7. An auto grid moving apparatus for an X-Ray imaging device, the apparatus comprising:
    an X-ray grid;
    a grid holder on which the X-ray grid is disposed;
    a fixing base;

a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move;

a sliding grid support apparatus, wherein the sliding grid support apparatus comprises a sliding grid support slider and a fixing guide rail base, wherein the sliding grid support slider is configured to slide into the guide rail base and wherein the grid holder is configured to slide bi-directionally with the sliding grid support slider;

a hard stopper at each of the two ends of the sliding grid support slider and a support block at the middle portion of the sliding grid support slider;

a fixing plate at the non-driving end of the X-Ray grid; and a hook at each of two ends of the fixing plate, wherein when the X-Ray grid moves, the hook at one end contacts with the support block at the middle portion of the sliding grid support slider, pushing the sliding grid support slider to slide on the guide rail base, thereby making at least half of the sliding grid support slider to move out together with the X-Ray grid.

8. The auto grid moving apparatus for X-Ray imaging device according to claim 7, wherein the support block comprises a screw or bolt.

9. The auto grid moving apparatus for X-Ray imaging device according to claim 7, wherein the hard stoppers comprise screws or bolts.

10. A bed of an X-Ray imaging device, the bed comprising:
a table;
an X-Ray detector holder housing disposed beneath the table;
table frames at two ends of the table; and
an auto grid moving apparatus located between the underneath of the table and the X-Ray detector holder housing, the auto grid moving apparatus comprising:
an X-ray grid;
a grid holder on which the X-Ray grid is disposed;
a fixing base fixed beneath the table;
a double sided timing belt geared with at least two timing wheels at the two ends of the timing belt on the inner side face of the timing belt and geared with the grid holder at the outer side face of the timing belt, wherein one of the timing wheels has a motor disposed thereon, the motor being configured to drive the timing wheel to move the timing belt and to drive the grid holder to move; and
semi-circular timing wheels fixed on the grid holder, wherein the outer side face of the timing belt is geared with the grid holder through the semi-circular timing wheels,
wherein the auto grid moving apparatus is configured to drive the X-Ray grid back and forth between the X-Ray detector housing and the table.

11. The bed of an X-Ray imaging device according to claim 10, wherein the auto grid moving apparatus further comprises a sliding grid support apparatus.

12. The bed of an X-Ray imaging device according to claim 11, wherein the sliding grid support apparatus comprises a sliding grid support slider and a fixing guide rail base, wherein the sliding grid support slider is configured to slide into the guide rail base and wherein the grid holder is configured to slide bi-directionally with the sliding grid support slider.

13. The bed of an X-Ray imaging device according to claim 12, wherein the sliding grid support slider is blocked by the table frame and automatically restores position when the sliding grid support slider reaches out of the guide rail base and the X-Ray detector housing reaches the end of the table.

* * * * *